United States Patent [19]

Grisar et al.

[11] Patent Number: 5,545,660

[45] Date of Patent: Aug. 13, 1996

[54] HYDRAZIDE DERIVATIVES OF 3,4-DIHYDRO-2H-1-BENZOPYRANS

[75] Inventors: J. Martin Grisar, Wissembourg; Margaret A. Petty, Strasbourg, both of France; Frank Bolkenius, Kehl, Germany

[73] Assignee: Merrell Pharmaceuticals Inc., Cincinnati, Ohio

[21] Appl. No.: 318,670

[22] PCT Filed: Mar. 12, 1993

[86] PCT No.: PCT/US93/02311

§ 371 Date: Oct. 6, 1994

§ 102(e) Date: Oct. 6, 1994

[87] PCT Pub. No.: WO93/20059

PCT Pub. Date: Oct. 14, 1993

[30] Foreign Application Priority Data

Apr. 7, 1992 [EP] European Pat. Off. ............ 92400972

[51] Int. Cl.⁶ ...................... A61K 31/355; C07D 311/72
[52] U.S. Cl. ............................. 514/458; 549/407
[58] Field of Search ..................... 549/407; 514/458

[56] References Cited

U.S. PATENT DOCUMENTS

| | | |
|---|---|---|
| 3,419,560 | 12/1968 | Bernstein et al. . |
| 3,947,473 | 3/1976 | Scott et al. . |
| 4,153,796 | 5/1979 | Hoehn . |
| 4,214,081 | 7/1980 | Krapcho . |
| 4,237,162 | 12/1980 | Kabbe et al. . |
| 4,321,270 | 3/1982 | Sundeen . |
| 4,617,317 | 10/1986 | Bennet . |
| 4,694,090 | 9/1987 | Shiono et al. . |
| 4,728,650 | 3/1988 | Eziri et al. . |
| 4,975,457 | 12/1990 | Rupprecht et al. . |

FOREIGN PATENT DOCUMENTS

| | | |
|---|---|---|
| 0236120 | 9/1987 | European Pat. Off. . |
| 0281261 | 9/1988 | European Pat. Off. . |
| 0293078 | 11/1988 | European Pat. Off. . |
| 0345593 | 12/1989 | European Pat. Off. . |
| 0369874 | 5/1990 | European Pat. Off. . |
| 0369083 | 5/1990 | European Pat. Off. . |
| 0387771 | 9/1990 | European Pat. Off. . |
| 0413668 | 2/1991 | European Pat. Off. . |
| 0550337 | 7/1993 | European Pat. Off. . |
| 0536036 | 9/1993 | European Pat. Off. . |
| 215778 | 9/1990 | Japan . |
| 9320057 | 10/1993 | WIPO . |
| 9320058 | 10/1993 | WIPO . |

OTHER PUBLICATIONS

Burger, Medicinal Chemistry, 2nd Edition, Interscience Publishers, Inc., New York, (1960) pp. 72–88.
Akkerman et al., J. Chem. Soc., Perkin Trans. I, No. 9, Sep. 1979, pp. 2119–2124.
Unanue et al., Text Book of Immunology, Williams & Wilkins, Baltimore, 1984, pp. 289–294.
Koyama et al., Chemical Abstracts, vol. 111, No. 13, 115639T (1989).

*Primary Examiner*—Nicky Chan
*Attorney, Agent, or Firm*—Carolyn D. Moon

[57] ABSTRACT

This invention relates to novel hydrazide acyl hydrazinium derivatives of certain 3,4-dihydro-2H-1-benzopyrans of the formula

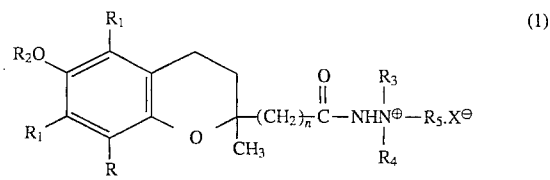

the stereoisomers and mixtures thereof, their inner salts, and the pharmaceutically acceptable salts thereof wherein R is H or $C_{1-6}$ alkyl, $R_1$ is $C_{1-6}$ alkyl, $R_2$ is H or —C(O)R, $R_3$ and $R_4$ are independently $C_{1-6}$ alkyl;

$R_5$ is $C_{1-6}$ alkyl, or

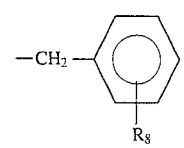

with $R_8$ being H or halogeno, n is zero, 1, 2, or 3 and is a halide, —S(O)₃R₆, or nothing when the inner salt is formed $R_6$ is H, $C_{1-6}$ alkyl, phenyl or 4-methylphenyl, to the intermediates, processes and techniques for their preparation, to their ability to manifest the property of being free radical scavengers, and to their end-use application in the treatment of disease conditions capable of being ameliorated by free radical scavengers.

13 Claims, No Drawings

HYDRAZIDE DERIVATIVES OF 3,4-DIHYDRO-2H-1-BENZOPYRANS

This is a 371 of PCT/US93/02311 filed Mar. 12, 1993.

This invention relates to novel hydrazide acyl hydrazinium derivatives of certain 3,4-dihydro-2H-1-benzopyrans, to the intermediates, processes and techniques for their preparation, to their ability to manifest the property of being free radical scavengers, and to their end-use application in the treatment of disease conditions capable of being ameliorated by free radical scavengers.

More specifically this invention relates to compounds of the formula

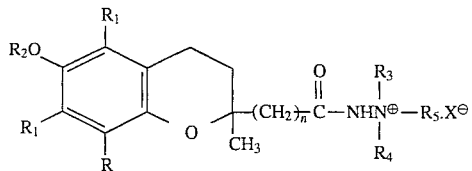

(1)

the stereoisomers and mixtures thereof, their inner salts, and the pharmaceutically acceptable salts thereof wherein R is H or $C_{1-6}$ alkyl, $R_1$ is $C_{1-6}$ alkyl, $R_2$ is H or —C(O)R, $R_3$ and $R_4$ are independently $C_{1-6}$ alkyl;

$R_5$ is $C_{1-6}$ alkyl, or

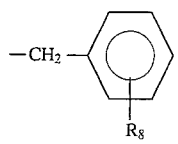

with $R_8$ being H or halogeno, n is zero, 1, 2, or 3 and

X is a halide, —S(O)$_3$R$_6$, or nothing when the inner salt is formed $R_6$ is H, $C_{1-6}$ alkyl, phenyl or 4-methylphenyl.

As used herein the term alkyl includes the straight or branched saturated aliphatic hydrocarbyl moieties having the designated number of carbon atoms, preferably methyl or ethyl, but including propyl, isopropyl, n-butyl, t-butyl, hexyl and the like. The term —C(O)R includes those acyl moieties wherein R includes H and $C_{1-6}$ alkyl, embracing formyl and methylcarbonyl as preferred species but including ethylcarbonyl and the like. In the acyl hydrazinium moiety (i.e., —C(O)NHN$^{\oplus}$($R_3$)($R_4$)($R_5$).X$^{\ominus}$) the $R_3$, $R_4$ and $R_5$ preferably are the same alkyl with methyl and ethyl being preferred and when $R_5$ is not alkyl the preferred radicals are benzyl or $R_8$-substituted benzyl moieties with $R_8$ preferably being chloro or bromo. The X$^{\ominus}$ moiety includes a halogen, preferably chloro or bromo, or a —S(O)$_3$R$_6$ moiety wherein $R_6$ is H, $C_{1-6}$ alkyl, phenyl, or, preferably, 4-methylphenyl.

The inner salts include those compounds wherein the acyl hydrazinium moiety would have the structure configuration

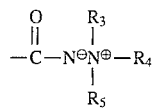

as its terminal moiety.

The compounds of the present invention include stereoisomers; the term "stereoisomer" is a general term for all isomers of individual molecules that differ only in the orientation of their atoms in space. It includes mirror image isomers (enantiomers), geometric isomers (cis/trans), and isomers of compounds with more than one chiral center that are not mirror images of one another (diastereoisomers).

In general, the compounds of this invention may be prepared by standard chemical processes and techniques analogously known in the art from materials which are either known per se or which may be prepared in an analogous manner. Preferably the starting materials are in the desired enantiomeric form. The overall process for the preparation of the compounds of this invention may be depicted by the following reaction scheme with the chemical process and techniques being taught by the specific examples herein described.

REACTION SCHEME A

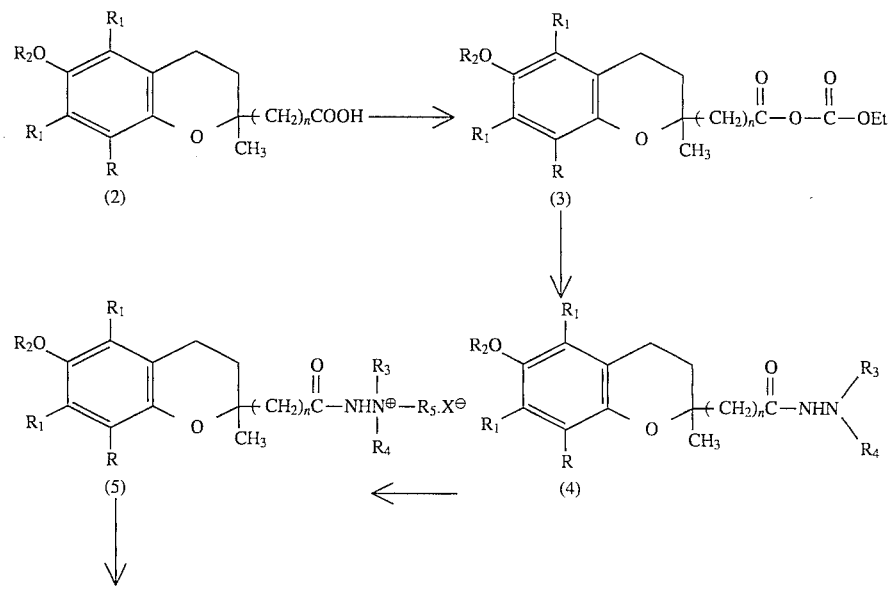

-continued
REACTION SCHEME A

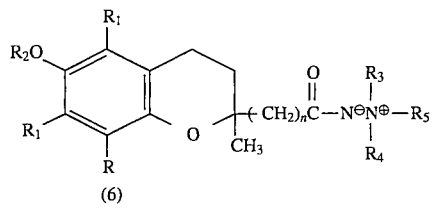
(6)

wherein R, $R_1$, $R_2$, $R_3$, $R_4$, $R_5$, n and X are as previously defined.

In essence, the reaction scheme entails the conversion of the acids (2) to a mixed anhydride (3) by reaction with ethylchloroformate at low temperatures (below 0° C.) under anhydrous conditions. The resulting mixed anhydrides are treated with an unsymmetrical dialkylhydrazine, preferably, at about room temperature to produce the hydrazides of formula (4). Upon reaction with the appropriate alkylhalide or alkylsulfonates (e.g. $R_5X$ wherein X is a halide or $SO_3R_5$) the hydrazide is converted to its corresponding acyl hydrazinium salt (5) and, by treatment with base, preferably sodium hydroxide, to the inner salt (6). Of course acylation of a hydroxy function at the 6-position of the 3,4-dihydrobenzopyran may be effected by reaction with an acid anhydride or acid halide to produce the desired formyl or alkylcarbonyloxy moieties. Conversion back to the 6-OH moiety may be effected by hydrolysis, said acylation and hydrolysis reaction being well known in the art.

The following examples illustrate the processes by which the compounds of this invention may be prepared.

EXAMPLE 1

2-[(3,4-Dihydro-6-hydroxy-2,5,7,8-tetramethyl-2H-1-benzopyran-2-yl)carbonyl]-1,1,1-trimethylhydrazinium 4-methylbenzenesulfonate

STEP A:

A solution of 10.0 g (0.04 m) of 3,4-dihydro-6-hydroxy-2,5,7,8-tetramethyl-2H-1-benzopyran-2 -carboxylic acid and 4.05 g (0.04 m) of triethylamine in 100 ml of dry tetrahydrofuran is cooled to −10° C. under conditions that exclude moisture (drying tube) and a solution of 4.34 g (0.04 m) of ethyl chloroformate in 50 ml of tetrahydrofuran is added at such a rate that the internal temperature does not rise above 0° C. After completed addition (about 15 minutes) the mixture is stirred at 0° C. for 35 minutes. Then, a solution of 2.40 g (0.04 m) of unsymmetrical dimethylhydrazine in 30 ml of tetrahydrofuran is added, the mixture is allowed to warm to room temperature and is stirred overnight. The solvent is evaporated under reduced pressure, water is added and the product is extracted with ethyl acetate. The extract is washed with water and sodium bicarbonate solution, dried over sodium sulfate, filtered and evaporated to give 9.24 g of an oil. It is crystallized and recrystalized from ethyl acetate/heptane to give 6.13 g of 3,4-dihydro-6-hydroxy-N',N',2,5,7,8-hexamethyl-2H-1-benzopyran-2-carboxhydrazide, m.p. 145°–146° C.

STEP B:

A solution of 5.58 g (0.01922 m) of the above dimethylhydrazide and 3.94 g (0.02114 m) of methyl p-toluenesulfonate in 60 ml of acetonitrile is refluxed for 6 hours. The mixture is allowed to cool overnight and crystalline material that formed is collected and recrystallized from acetonitrile/water to give 6.52 g of the title compound, m.p. 244° C. (decomposition). Elemental analysis, UV, IR and $^1$H-NMR spectra confirm the structure.

EXAMPLE 2

2-[(3,4-Dihydro-6-hydroxy-2,5,7,8-tetramethyl-2H-1-benzopyran-2-yl)carbonyl]-1,1,1-trimethylhydrazinium, inner salt To a solution of 3.0 g (0.00627 m) of the compound described in Example 1 in 10 ml of water and 10 ml of ethanol is added 3.2 ml of 2N NaOH. The solution is evaporated to dryness and the residue is slurried in 15 ml of water. The solid is collected and is recrystallized twice from water to give the title compound, m.p. 187° C. (decomposition).

EXAMPLE 3

2-{3,4-Dihydro-6-hydroxy-2,5,7,8-tetramethyl-2H-1-benzopyran-2-acetyl)-1,1,1-trimethylhydrazinium 4-methylbenzenesulfonate Using the procedure described in Example 1 but starting with 3,4-dihydro-6-hydroxy-2,5,7,8-tetramethyl-2H-1-benzopyran-2-acetic acid gives the dimethylhydrazide derivative of that acid, m.p. 151°–152° C.

Treatment with 10% excess methyl p-toluenesulfonate in refluxing acetonitrile, as described in Example 1, gives the title compound, m.p. 182°–183° C.

EXAMPLE 4

2-(3,4-Dihydro-6-hydroxy-2,5,7,8-tetramethyl-2H-1-benzopyran-2-acetyl)-1,1,1-trimethylhydrazinium, inner salt Treatment of the tosylate described in the preceding example with an equivalent of base, as described in Example 2, gives the internal salt, m.p. 219° C. (decomposition). Elemental analysis, UV, IR and $^1$H-NMR spectra confirm the structure.

EXAMPLE 5

Resolution of 2S(−)- and 2R-(+)-2-(3,4-dihydro-6-hydroxy-2,5,7,8-tetramethyl-2H-1-benzopyran-2-acetyl)-1,1,1-trimethylhydrazinium 4-methylbenzenesulfonate and inner salt Step A:

Resolution of 3,4-Dihydro-6-hydroxy-2,5,7,8-tetramethyl-2H-1-benzopyran-2-acetic Acid To a hot solution of 132.16 g of the title compound in 700 ml of isopropanol is added 60.59 g of S-(–)-α-methylbenzylamine and 100 ml of ethyl acetate. Slow crystallization overnight in a refrigerator gives somewhat more than half the theoretical amount of crystalline material (checked by evaporating the filtrate to dryness). This material is recrystallized in a like manner three times and the resulting pure diastereomeric salt is converted to free acid by shaking in 200 ml of 2N hydrochloric acid and 400 ml of ethyl acetate. The aqueous phase is separated and extracted with ethyl acetate. The combined organic phase is washed with 2N hydrochloric acid, water, and a saturated sodium chloride solution, dried over anhydrous sodium sulfate, filtered and evaporated to dryness. The resulting solid is recrystallized from ethyl acetate/heptane to give 40.85 g (62%) of the S-(–)-enantiomer of the title compound, $[\alpha]_D^{25}=-9.61°$ (0.95% in MeOH) The enantiomeric purity, as determined by HPLC is ee=99.9%. Elemental analysis was within 0.3% of theory.

The combined filtrates of the above diastereomeric salt crystallizations are evaporated and converted to free acid as described to give 92.02 g of material. It is dissolved in 600 ml of isopropanol and 42.19 g of R-(+)-α-methylbenzylamine is added as well as 200 ml of ethyl acetate. Slow crystallization and two recrystallizations give, after conversion to free acid and one final recrystallization, 41.50 g (63%) of the R-(+)-enantiomer of the title compound $[\alpha]_D^{25}=+9.35°$ (0.96% in MeOH) ee=99.9%. Anal C,H.

It is possible to recover the unresolved balance of material from the filtrates as well as the enantiomeric amines for use in a subsequent resolution.

STEP B:

Using the procedure described in Examples 1 and 3, but starting with the 2S-(–)- and 2R-(+)-enantiomers of the acid described in Example 5, Step A, gives the 4-methylbenzenesulfonates of the two enantiomers of the title compound.

These 4-methylbenzenesulfonate salts are converted to the inner salts by the procedure described in Examples 2 and 4 to give the two enantiomers of the title compound, $[\alpha]_D^{25}=+2.30°$ and $-3.07°$ respectively (1% in MeOH).

The compounds of this invention are free radical scavengers. Free radical reactions have been implicated in the pathology of more than 50 human diseases. Radicals and other reactive oxygen species are formed constantly in the human body both by deliberate synthesis (e.g. by activated phagocytes) and by chemical side-reactions. They are removed by enzymic and non-enzymic antioxidant defence systems. Oxidative stress, occurring when antioxidant defences are inadequate, can damage lipids, proteins, carbohydrates and DNA. A few clinical conditions are caused by oxidative stress, but more often the stress results from the disease and can make a significant contribution to the disease pathology. For a more detailed review see B. Halliwell in *Drugs*, 1991, 42, 569–605.

When the blood supply to parts of the heart muscle is blocked, a myocardial infarct (heart attack) results and the deprived muscle tissue dies with the result of permanent heart damage. If the blood supply can be re-established within hours after ischemia, the heart muscle tissue remains viable and permanent damage can be reduced. This can be accomplished by surgical as well as pharmacologic (thrombolysis) procedures and these processes are known as reperfusion.

Ischemia followed by reperfusion causes formation of oxygen-derived free radicals and increased lipid peroxidation and results in tissue injury. Administration of free radical scavengers to animals subjected to coronary infarction/reperfusion or ischemia/reperfusion or surgical interventions/reperfusion reduces these effects in heart, lung, kidney, pancreas, brain and other tissues.

Reperfusion is now widely and successfully applied and it has been claimed that fatalities due to myocardial infarction can be reduced by 20–30%. However, reperfusion also poses problems. Oxygen-deprived (ischemic) tissue finds itself in an abnormal state and is vulnerable when suddenly exposed to oxygen-rich blood. This has been termed the "oxygen paradox" and leads to reperfusion damage in the form of cell death. It has been postulated that this damage is due to oxygen-derived free radicals. Evidence for this hypothesis has been obtained in animal experiments. B. R. Lucchesi and coworkers showed that the enzyme superoxide dismutase, as well as the free radical scavenger N-(mercaptopropionyl)-glycine reduce canine myocardial reperfusion injury (Cir. Res., 1984, 54, 277–285; J. Cardiovasc. Pharmacol., 1986, 8, 978–88; Fed. Proc., 1987, 46, 2413–21).

Vitamin E, i.e., α-tocopherol, a well known compound of the formula

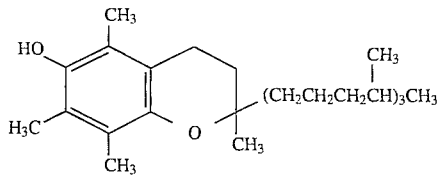

is a natural anti-oxidant that reacts with oxygen-derived free radicals as well as hydrogen peroxide. It has been shown that it is intercalated in lipid membranes and that its biological function is to protect biomembranes against oxidative attack. The anti-oxidant 3,4-dihydro-2,5,7,8-tetramethyl-2 H-2-benzopyran-6-ol moiety of α-tocopherol is constantly regenerated by the ubiquitous redox systems.

The compounds of the present invention are also useful in treating the process of inflammation which is known to involve the release of superoxide radicals from phagocytic cells which cause some of the symptoms of rheumatoid arthritis and other inflammatory diseases such as ulcerative colitis and inflammatory dermatological disorders such as psoriasis. Of particular use of this anti-inflammatory effect of the compounds of this invention is the treatment of inflammatory lower bowel disease.

Inhalation injury of the lungs is typically caused by heat and chemical irritation, and chemical injury is the leading lethal cause of smoke inhalation injury. Smoke inhalation leads to lung injury due to an increase in pulmonary microvasculature and pulmonary edema. This process is accompanied by increased lipid peroxidation in lung tissue. An inhibitor of lipid peroxidation was shown to reduce these symptoms in animals subjected to hot sawdust smoke by Z. Min et al., (*J. Med. Cell. PLA*, 1990, 5, 176–180). They suggest the use of antioxidants in treatment of smoke inhalation-lung injury, adult respiratory distress syndrome and emphysema.

Reactive oxygen species also play a role in the formation of foam cells in atherosclerotic plaques (reviewed by D. Steinberg et al., *New Engl. Med.*, 1989, 320, 915–924) and the free radical scavenger probucol has a marked antiatherosclerotic effect in hyperlipidemic rabbits (Carew et al., *Proc. Nat. Acad. Sci. USA*, 1987, 84, 7725–7729. Degenerative retinal damage and diabetogenic retinopathy have also been listed as target for treatment with free radical scavengers (cf. J. W. Baynes, *Diabetes*, 1991, 40, 405–412; S. P. Wolff et al., *Free Rad. Biol. Med.*, 1991, 10, 339–352).

The compounds may also be useful in the treatment of cancers, and degenerative diseases related to aging, stroke, and head trauma, since oxygen-derived free radicals have been identified among causative factors. For reviews, see B. Halliwell and C. Gutteridge, Biochem. J., 1984, 219, 1–14; TINS 1985, 22–6. Antioxidants have also been shown to be useful in the treatment of cataracts, *Free Rad. Biol. Med.*, 12:251–261 (1992).

In vitro and in vivo activity for the compounds of this invention may be determined by the use of standard assays which demonstrate the free radical scavenging property, affinity for cardiac tissue and cardioprotective properties, as well as by comparison with agents known to be effective for these purposes.

Exemplary of the assay useful for determining the free-radical scavenging property of the compounds of this invention is by the in vitro inhibition of lipid peroxidation in rat brain homogenates.

The free radical scavenging properties of the compounds may readily be evaluated wherein superoxide radicals are generated by 4 mU of xanthine oxidase in the presence of 0.1 mM xanthine and detected by reduction of 40 µM nitro blue tetrazolium (NBT) to the diformazan dye in a spectrophotometric assay as described by C. Beauchamp and I. Fridovick, (*Analyt. Biochem.* 1971, 44, 276–287). 30 U of superoxide dismutase inhibited this reduction by 90% which is due to superoxide radicals. In the presence of a superoxide scavenger (test compound) there is a competition for the superoxide radical and thus a reduction in the color formation of NBT demonstrates the superoxide radical scavenging property of the test compound.

Inhibiting the process of lipid peroxidation may be assayed using tissue homogenates for measuring the antioxidant activity of biological fluids by the methodology of J. Stocks et al., (*Clin. Sci. Mol. Med.*, 1974, 47, 215–222), wherein a brain tissue homogenate of treated adult Sprague Dawley rats is utilized. Samples of total volume 1 ml of diluted brain homogenate and with the scavenger at an appropriate dilution are incubated. Non-incubated samples are taken as background. Controls are run without scavenger and a sample containing only buffer is taken as blank. After incubation at 37° C. for 30 minutes, 200 µl of 35% perchloric acid is added, the samples centrifuged and 800 µl of the supernatants mixed with 200 µl of 1% thiobarbituric acid. The pink condensation product of thiobarbituric acid reactive material is developed at 100° C. in a boiling water bath for 15 minutes, and absorbance read at 532 nm.

For ex vivo inhibition of tissue including heart tissue, lipid peroxidation in mice may be utilized to demonstrate the ability of the compounds to penetrate and act as free radical scavengers in these tissues. This assay involves pretreatment of male CD1 mice by subcutaneous administration of the test compound. One hour later the tissues are excised, homogenized 1+9 (w/v) in 20 mM potassium phosphate buffer at pH 7.3 (0.14M KCl) and incubated at 1/100 concentration in 1 ml of buffer at 37° C. for 30–120 minutes. At the end of the incubation 200 µl of 35% perchloric acid is added and proteins removed by centrifugation. To 800 ml of the supernatant are added 200 µl of 1% TBA and the samples are treated to 100° C. for 15 minutes. The TBA adduct is extracted into 2 times 1 ml of n-butanol. The fluorescence is measured at an excitation wavelength of 515 nm and an emission wavelength of 553 nm against a standard prepared from malondialdehyde dimethylacetal.

Stimulated human leukocytes release radicals and other oxygen metabolites, which, during inflammation, act as microbial agents. At the same time, they release proteolytic enzymes, such as elastase, which are also microbicidal but potentially threaten the connective tissue of the host. An endogenous $\alpha_1$-proteinase inhibitor ($\alpha_1$Pi) normally protects the host tissue from proteolytic digestion. $\alpha_1$Pi is however, inactivated by the leukocyte-derived oxidants. Antagonism of the inactivation of $\alpha_1$Pi is an indication of the disclosed radical scavengers. The concentration needed to protect 50% of the elastase inhibitory capacity of $\alpha_1$Pi ($PC_{50}$) depends on the amount of stimulated leukocytes present.

Method: The procedure described by Skosey and Chow was followed (see J. L. Skosey and D.C. Chow in *Handbook of Methods for Oxygen Radical Research* (Greenwald, R. A., ed.) 1985, pp.413–416, CRC Press, Boca Raton). In short, human $\alpha_1$Pi was incubated with zymosan-stimulated human peripheral-blood leukocytes in the absence or presence of the scavengers. The amount of $\alpha_1$Pi protected from oxidative inactivation was determined by its residual elastase inhibitory capacity.

The relevance to inflammation matter has been reviewed by Weiss (see S. J. Weiss, *N. England Med.*, 1989, 320, 365–376). Lung emphysema is associated with a genetic defect in $\alpha_1$Pi; the disease is further enhanced by oxidants inhaled during cigarette smoking, which leads to oxidative inactivation of $\alpha_1$Pi in the lung tissue (see J. Travis and G. S. Salvesen, *Annu. Rev. Biochem.*, 1983, 52, 655–709). Oxidized $\alpha_1$Pi has also been isolated from rheumatoid synovial fluid (see P. S. Wong and J. Travis, *Biochem. Biophys. Roc. Commun.*, 1980, 06, 1440–1454). The degradation of hyaluronic acid, a macromolecule accounting for the viscosity of synovial fluid, is triggered by superoxyl radicals released from human leukocytes in vitro (see R. A. Greenwald and S. A. Moak, *Inflammation*, 1986, 10, 15–30). Furthermore, nonsteroidal anti-inflammatory drugs were shown to inhibit the release of superoxyl radicals from leukocytes (see H. Strom and I. Ahnfelt-Ronne, *Agents and Actions*, 1989, 26, 235–237 and M. Roch-Arveiller, V. Revelant, D. Pharm Huy, L. Maman, J. Fontagne, J. R. J. Sorenson and J. P. Giroud, *Agents and Actions*, 1990, 31, 65–71), and 5-aminosalicylic acid may exert its therapeutic activity in inflammatory bowel disease by a radical scavenger mechanism (see I. Ahnfelt-Ronne, O. H. Nielsen, A. Christensen, E. Langholz, V. Binder and P. Riis, *Gastroenterology*, 1990, 98, 1162–1169). Therefore, it is believed that the compounds of this invention may be useful in the mentioned pathologic situations and that inflammatory bowel disease may be a special target. An immune stimulatory effect of antioxidants has also been reported in that they enhanced lymphocyte activity (R. Anderson and P. T. Lukey, *Ann. N.Y. Acad. Sci.*, 1987, 498, 229–247) in vitro in the presence of triggered leukocytes, and ex vivo after pretreatment of human volunteers.

Thus, using standard and well known methodology, as well as by comparison with known compounds found useful, it is to be found that the compounds are free radical scavengers useful in the prevention and treatment of such disease states related to neurotoxicity due to excessive glutamic acid release, to Huntington's disease, Alzheimer's disease and other cognitive dysfunctions, (e.g. memory, learning and attention deficits), amnesia, and Parkinson's disease, as well as the treatment and prevention of tissue damage in heart, lung, kidney, pancreas and brain tissues induced by ischemia/reperfusion, surgical intervention and infarction/reperfusion and to allay acute blood loss due to hemorrhagic shock.

The compounds of this invention are related to a-tocopherol and also possess a 3,4-dihydro-6-hydroxy-2,5,7,8-tetraalkyl-2H-1-benzopyran-2-yl moiety, but the 2-position lipophylic moiety of the α-tocopherol molecule, which is thought to be responsible for its ubiquitous incorporation into biomembranes, is replaced with a hydrophilic moiety to impart a greater affinity for cardiac tissue. Thus, the compounds of this invention are also useful as pharmacologic antioxidants and free radical scavengers and, in particular, as scavengers of superoxide anion radical $O_2^-$. They can be therapeutically employed where reperfusion damage due to oxygen-derived free radicals and hydrogen peroxide causes cell death in tissues. This situation arises when total or partial blockade of blood supply to tissues is removed, either spontaneously (transient ischemia) or by pharmacologic or surgical intervention (thrombolysis, angioplasty, by-pass, organ transplant and the like). Tissues subjected to transient ischemia or reperfusion in various disease states, or by their medical treatment, are those of heart, lung, kidney, pancreas and brain. In particular, the now rapidly increasing practice of pharmacologic thrombolysis, also known as reperfusion, after coronary infarct and stroke, will benefit by prior or concomitant administration of a free radical scavenger such as the compounds of this invention. Similarly, surgical interventions, such as percutaneous transluminal coronary angioplasty, where a dilating balloon is used to increase the luminal diameter in severely occluded atherosclerotic vessels, coronary by-pass operations, and organ transplant surgery create conditions where reperfusion damage due to oxygen-derived radicals takes place and can be reduced by scavengers. Transient ischemia is one of the causative factors that lead to angina pectoris, and thus the compounds of this invention are also useful as antianginal agents.

The compounds of this invention may also be evaluated in ligation-induced infarcted and reperfused rats as follows. One of two groups of rats is infused intravenously with a solution of a test compound in saline at a rate of 2.3 ml/h (10 mg/kg/h). The control group is infused with saline at the same rate. After 10 minutes of drug infusion, coronary arteries are ligated surgically for 60 minutes, ligation is loosened to allow reperfusion for 30 minutes. The ligation is retied and a dye (Evans Blue) is injected. The animals are sacrificed and the heart ventricles are removed and weighed. The unstained tissue is dissected and weighed; this represents the "area at risk", i.e. the area that is deprived of blood supply by ligation. To determine the infarcted area, the tissue is incubated with 2,3,5-triphenyltetrazolium chloride. Infarcted tissue becomes light colored and can be dissected and weighed. Thus, for each rat that survives the ligation a measurement of "area at risk" (RA) and of "infarcted area" (IA) is obtained and the ratio IA/RA is calculated.

The compounds of this invention can be utilized both prophylactically and therapeutically. The amount of active ingredient for therapeutic administration can vary over a wide range and is dependent upon such factors as the species of patient to be treated, its age, health, sex, weight, nature and the severity of the condition being treated. The term "patient" refers to a warm-blooded animal such as, for example, rats, mice, dogs, cats, guinea pigs, primates, and humans. Generally, a therapeutically effective amount of the active ingredient to be administered will range from about 0.1 mg/kg to 30 mg/kg of body weight per day. For prophylactic administration, corresponding lower doses can be utilized. Preferably, the compounds of the present invention will be administered to the patient in combination with a pharmaceutically acceptable carrier which is any substance which aids in the administration of the compound without substantially affecting its therapeutic properties.

Most preferably, the compounds are administered intravenously particularly under crisis situations wherein it is essential that the therapeutic agent be gotten to its site of action as quickly as possible, such as in those emergency conditions caused by coronary infraction, stroke and surgical interventions, conditions which can cause severe reperfusion damage.

The compounds of this invention also can be orally administered, preferably using more active ingredient per day than when parenterally administered, preferably taking divided doses 3 to 4 times per day. Preferably, enteral administration in post "crisis" situations, particularly after release from hospitalized conditions. The compounds can be used in standard dosage unit forms such as tablets, capsules, dragees, lozenges, elixirs, emulsions, suspensions, and in cases wherein topical application is preferred by suppository or sub-lingual administration. Tablets and capsules containing from 100 to 400 mg of active ingredient are preferred modes of enteral administration. Of course, in the treatment of inflammation the preferred method of administration is by depot injection directly to the situs of the inflammation area with follow-up enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the aesthetic qualities of the tablets and make them more acceptable to the patient. For its own effects as an anti-oxidant, ascorbic acid also is advantageously utilized in formulations with the active ingredients of formula (1).

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polyethylene glycol solutions. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. In certain topical and parenteral preparations, various oils can be utilized as carriers or excipients. Illustrative of such oils are mineral oils, glyceride oils such as lard oil, cod liver oil, peanut oil, sesame oil, corn oil and soybeam oil. For insoluble compounds, suspending agents may be added as well as agents to control the viscosity, as for example, magnesium aluminum silicate or carboxymethylcellulose. In addition to these excipients, buffers, preservatives and emulsifying agents may also be added. Typical enema preparation of the retention type enema utilize small volumes, generally much less than about 150 mL for an adult, typically volumes of only a few milliliters are preferred. Excipients and solvents for use in retention anemas should, of course, be selected so as to avoid colonic irritation and should also be selected so as to minimize absorption of the various agents.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compounds of the present invention may be incorporated into an aerosol preparation by means commonly known to those skilled in the art. The aerosol preparation may be prepared for use as a topical aerosol or may be prepared for inhalation. The aerosol preparation may be in the form of a solution or suspension and may contain other ingredients such as solvents, propellants and/or dispersing agents. Typical examples of aerosol preparations are shown in *Remington's Pharmaceutical Sciences*, 18th ed., Mack Publishing Company, Easton Pa., pp. 1694–1712(1990) incorporated herein by reference.

Of course, as is true in most instances wherein certain classes of chemical compounds have been found to have beneficial therapeutic end-use applications, certain sub-generic groups and certain specific compounds are preferred. In this instance the preferred compounds of Formula I are those wherein $R_3$, $R_4$ and $R_5$ are each methyl; R is methyl; each $R_1$ is methyl, $R_2$ is hydrogen; n is zero or one; and/or X is 4-methylbenzenesulfonate or nothing when the inner salt is formed.

What is claimed is:

1. A compound of the formula

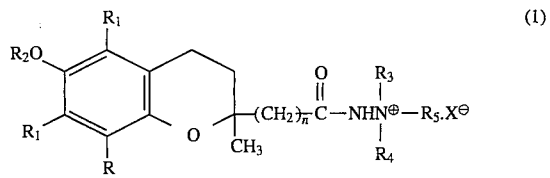

the stereoisomer or mixture thereof, inner salt, or the pharmaceutically acceptable salt thereof wherein R is H or $C_{1-6}$ alkyl, $R_1$ is $C_{1-6}$ alkyl, $R_2$ is H or —C(O)R, $R_3$ and $R_4$ are independently $C_{1-6}$ alkyl;

$R_5$ is $C_{1-6}$ alkyl, or

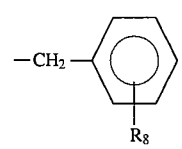

with $R_8$ being H or halogeno, n is zero, 1, 2, or 3 and

X is a halide, —S(O)$_3R_6$, or nothing when the inner salt is formed $R_6$ is H, $C_{1-6}$ alkyl, phenyl or 4-methylphenyl.

2. A compound of claim 1 wherein each of $R_3$, $R_4$ and $R_5$ are methyl.

3. A compound of claim 1 wherein each of $R_1$ are methyl.

4. A compound of claim 1 wherein X is —S(O)$_3R_6$.

5. A compound of claim 1 wherein X is nothing.

6. A compound of claim 1 wherein $R_2$ is hydrogen.

7. The compound of claim 1 wherein the compound is 2-[(3,4-dihydro-6-hydroxy-2,5,7,8-tetramethyl-2H-1-benzopyran-2-yl)carbonyl]-1,1,1-trimethylhydrazinium 4-methylbenzenesulfonate or enantiomer thereof.

8. The compound of claim 1 wherein the compound is 2-[(3,4-dihydro-6-hydroxy-2,5,7,8-tetramethyl-2H-1-benzopyran-2-yl)carbonyl]-1,1,1-trimethylhydrazinium, inner salt or enantiomer thereof.

9. The compound of claim 1 wherein the compound is 2-(3,4-dihydro-6-hydroxy-2,5,7,8-tetramethyl-2H-1-benzopyran-2-acetyl)-1,1,1-trimethylhydrazinium, 4-methylbenzenesulfonate or enantiomer thereof.

10. The compound of claim 1 wherein the compound is 2-(3,4-dihydro-6-hydroxy-2,5,7,8-tetramethyl-2H-1-benzopyran-2-acetyl)-1,1,1-trimethylhydrazinium, inner salt or enantiomer thereof.

11. A pharmaceutical composition comprising a compound of claim 1 and a pharmaceutically acceptable carrier.

12. A method of treating a patient for reperfusion damage by administering an effective amount of a compound of claim 1.

13. A method of treating a patient for inflammatory bowel disease by administering an effective amount of a compound of claim 1.

* * * * *

UNITED STATES PATENT AND TRADEMARK OFFICE
CERTIFICATE OF CORRECTION

PATENT NO. : 5,545,660

DATED : August 13, 1996

INVENTOR(S) : J. Martin Grisar et al.

It is certified that error appears in the above-indentified patent and that said Letters Patent is hereby corrected as shown below:

Column 5, line 47 of the patent reads "defence" and shoud read -- defense --.

Column 5 line 49 of the patent reads " defences" and should read -- defenses --.

Column 6, line 60 of the patent reads " Engl. Med." and should read -- Engl. J. Med. --.

Column 8, line 20 of the patent reads " Engl. Med." and should read -- Engl. J. Med. -- .

Column 8, line 65 of the patent reads " a-" and should read -- a- -- .

Column 11, line 4 of the patent reads "anemas" and should read -- enemas --.
Abstract of the patent reads "and is a halide" and should read -- and X is halide --.

Signed and Sealed this

Twenty-eighth Day of October, 1997

*Attest:*

BRUCE LEHMAN

*Attesting Officer*      *Commissioner of Patents and Trademarks*